United States Patent
Carlson et al.

(10) Patent No.: US 11,340,206 B2
(45) Date of Patent: May 24, 2022

(54) PRESSURE COMPENSATED PH SENSOR

(71) Applicant: Sea-Bird Electronics, Inc., Bellevue, WA (US)

(72) Inventors: Daryl Allen Carlson, Seattle, WA (US); Jesse John Bauman, Woodinville, WA (US); David Dahl Walter, Stanwood, WA (US); Matthew Eric D'Asaro, Seattle, WA (US)

(73) Assignee: Sea-Bird Electronics, Inc., Bellevue, WA (US)

(*) Notice: Subject to any disclaimer, the term of this patent is extended or adjusted under 35 U.S.C. 154(b) by 230 days.

(21) Appl. No.: 16/545,351

(22) Filed: Aug. 20, 2019

(65) Prior Publication Data
US 2020/0057043 A1 Feb. 20, 2020

Related U.S. Application Data

(60) Provisional application No. 62/719,858, filed on Aug. 20, 2018.

(51) Int. Cl.
*G01N 33/18* (2006.01)
*G01N 27/30* (2006.01)
(Continued)

(52) U.S. Cl.
CPC ......... *G01N 33/1886* (2013.01); *G01N 27/28* (2013.01); *G01N 27/30* (2013.01); *G01N 27/4167* (2013.01)

(58) Field of Classification Search
CPC ........... G01N 33/1886; G01N 27/4167; G01N 27/283; G01N 27/4165
See application file for complete search history.

(56) References Cited

U.S. PATENT DOCUMENTS 3,652,439 A * 3/1972 Ben-Yaakov ......... G01N 27/30
204/279
4,783,252 A 11/1988 Benton
(Continued)

FOREIGN PATENT DOCUMENTS

| DE | 202006017215 U1 * | 2/2007 | ........... G01N 27/283 |
| EP | 1241471 A1 * | 9/2002 | ........... G01N 27/301 |
| JP | 61075254 A * | 4/1986 | ............. G01N 27/28 |

OTHER PUBLICATIONS

International Searching Authority, Notification of Transmittal of the International Serch Report and the Written Opinion of the International Searching Authority, or the Declaration, dated Oct. 31, 2019, pp. 16.

(Continued)

*Primary Examiner* — Herbert K Roberts
*Assistant Examiner* — Fatemeh Esfandiari Nia
(74) *Attorney, Agent, or Firm* — Ference & Associates LLC

(57) ABSTRACT

An embodiment a pressure compensated pH sensor apparatus, including: a pH sensing component comprising a sensing portion that is exposed to a fluid source when in use; a pressure chamber located in a position under the sensing portion and that surrounds all of the sensing portion not exposed to the fluid source when in use; and a pressure compensation mechanism located within the pressure chamber, wherein the pressure compensation mechanism reacts to pressure from an environment outside the apparatus, thereby support the sensing portion.

18 Claims, 4 Drawing Sheets

(51) Int. Cl.
*G01N 27/28* (2006.01)
*G01N 27/416* (2006.01)

(56) References Cited

U.S. PATENT DOCUMENTS

| | | | | |
|---|---|---|---|---|
| 6,423,197 | B1* | 7/2002 | Lenferink | G01N 27/4035 |
| | | | | 204/435 |
| 2003/0206026 | A1* | 11/2003 | Diakonov | E21B 49/08 |
| | | | | 324/723 |
| 2011/0147213 | A1* | 6/2011 | Auerswald | G01N 27/36 |
| | | | | 204/415 |
| 2013/0334044 | A1* | 12/2013 | Brown | G01N 27/414 |
| | | | | 156/257 |
| 2017/0299546 | A1* | 10/2017 | Rutz | G01N 27/4161 |
| 2018/0180574 | A1* | 6/2018 | Paul | G01N 27/40 |
| 2021/0096098 | A1* | 4/2021 | Scaboo | B01F 35/2142 |

OTHER PUBLICATIONS

Kangfa Deng et al:"Miniaturized force-compensated hydrogel-based pH sensors", Sensors and Actuators B: Chemical, vol. 255, Feb. 1, 2018 (Feb. 1, 2018), pp. 3495-3504.

Volker Schulz et al: "A Closed-Loop Hydrogel-Based Chemical Sensor", IEEE Sensors Journal, IEEE Service Center, New York, NY, US, vol. 13, No. 3, Mar. 1, 2013 (Mar. 1, 2013), pp. 994-1002.

* cited by examiner

PRESSURE COMPENSATED PH SENSOR

CLAIM FOR PRIORITY

This application claims priority to U.S. Provisional Application No. 62/719,858 filed on Aug. 20, 2018, entitled "PRESSURE COMPENSATED pH SENSOR", which is incorporated by reference herein in its entirety.

FIELD

This application relates generally to pH measurement of an aqueous sample, and, more particularly, to pH measurement of an aqueous sample using a pressure compensated sensor.

BACKGROUND

Ensuring water quality is critical to the health and well-being of humans, animals, and plants, which are reliant on water for survival. One parameter of water that may be measured is the pH. The measurement of pH of an aqueous sample is critical in a number of industries such as pharmaceuticals, biomedical, water supply, and other manufacturing fields. Measurement of pH may allow for proper treatment of water or ensuring proper water quality for sensitive purposes, and allows for identifying the overall quality of the water. Another important application of pH is in scientific studies of natural water including oceans, lakes, rivers, and estuaries.

BRIEF SUMMARY

One embodiment provides a pressure compensated pH sensor apparatus, comprising: a pH sensing component comprising a sensing portion that is exposed to a fluid source when in use; a pressure chamber located in a position under the sensing portion and that surrounds all of the sensing portion not exposed to the fluid source when in use; and a pressure compensation mechanism located within the pressure chamber, wherein the pressure compensation mechanism reacts to pressure from an environment outside the apparatus, thereby support the sensing portion.

Another embodiment provides a pressure compensated pH sensor probe, comprising: a pH sensing component comprising a sensing portion that is exposed to a fluid source when in use; a reference component; a pressure chamber fluidly located between the sensing portion and the reference component; a pressure compensation mechanism fluidly communicating with the pressure chamber, the sensing portion, and the reference component, wherein the pressure compensation mechanism reacts to pressure from an environment outside the apparatus, thereby supporting both reference component and the sensing portion.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
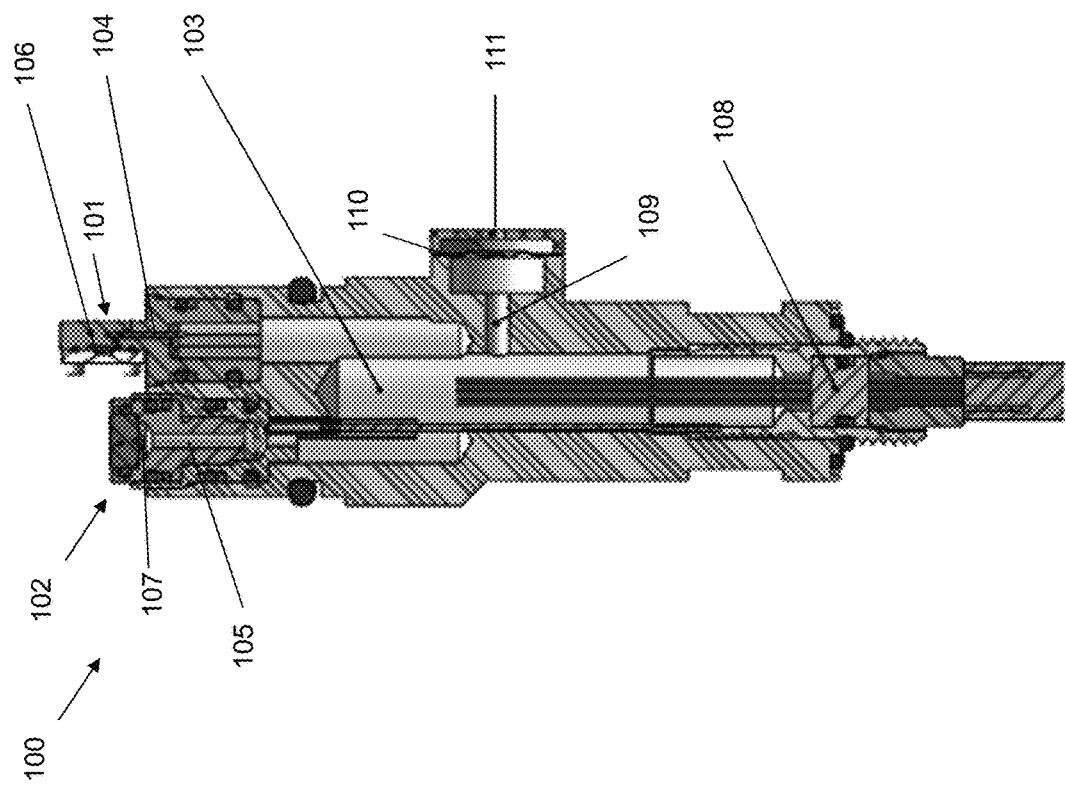
FIG. 1 illustrates an example pressure compensated pH sensor module.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Measuring fluid characteristics is important to determine the quality of the fluid. One characteristic that is commonly measured is the pH of the fluid. The pH gives many indicators regarding the quality of the fluid. Some fluids that need to be measured are located in environments having a pressure greater than the pressure found at sea level. For example, a sensor may be located deep in the ocean where the pressure around the sensor can be much greater than the environmental pressure at sea level. As another example, a sensor may be located within a machine or instrument that keeps the environmental pressure at an environmental pressure greater than that found at sea level.

At greater environmental pressures mechanical components tend to move and shift. Specifically, the higher pressures may cause parts of the component to move from the natural state of the component as found when at a sea level environmental pressure. This shift or movement of the component may cause issues with some sensors. For example, some pH sensors are built with a silicon sensing component that is exposed to the fluid and which allows for measurement of the desired characteristic. This silicon component is thin and fragile. The environmental pressures that are found at deep ocean depths where the sensor can be deployed cause the silicon to bend. The bending of the sensing element causes measurement results that are inaccurate.

Current techniques to counteract the inaccurate measurement results include calibration of the sensing element. To perform these calibrations a representative sensing element is exposed to the environmental pressures over multiple cycles. The measurement results are recorded and then normalized against the known expected results. The remaining sensing elements in the group represented by the representative element are then associated with the calibration results that were obtained with the representative sensing element. As these sensing elements are used in the field, the measurement results are continually updated using the representative calibration results to compensate for the bending and warping seen at the environmental pressures of the field.

The problem with such a calibration technique is that support structures that are created or provided by different manufacturers each have to be calibrated in separate batches. The support structure is the plastic, for example, PEEK, or other material, that is used to support the sensing elements. These support structures are highly variable in the manufacturing process. For example, the smoothness of the surface varies, the composition varies, the shape varies, and the like. Additionally, even among a single batch from a single manufacturer, the sensing elements do not behave in exactly the same way due to the differences in the shape and surface roughness of the support structure. Thus, the calibration that is obtained from a representative sensing element will not be accurate across all sensing elements of the batch, thereby resulting in measurements that are inaccurate or requiring each sensor to be separately calibrated. Additionally, performing calibration of the sensing elements is time and resource consuming. Also, the calibration results have to be programmed into the measurement device or other system so that the end measurement results are compensated and provide as accurate as possible results. Thus, a user has to make sure to program the correct calibration into the system. If the wrong calibration is programmed, the resulting measurements could be completely inaccurate.

Accordingly, an embodiment provides a system and method for compensating for environmental pressures without using a complex pressure calibration process. Rather, the described system and methods employ a sensor module that is pressure compensated, and may only need to be calibrate each sensor only a single time or not at all. One embodiment of the sensor module includes a fluid reservoir that holds pressure compensation fluid. The sensor module also includes a fluid chamber that is located directly under the sensing element. As the environmental pressure increases, this pressure is transferred to the fluid reservoir through a pressure port that is exposed to the environment. As the pressure in the fluid reservoir increases, the fluid is transferred to the fluid chamber that then supports the sensing element. In this way, the sensing element, even though it is exposed to the environmental pressure, is equally supported across the entire sensing element, thereby not allowing any portion of the sensing element to bend or warp due to the environmental pressures. In one embodiment, the sensing element is part of a larger pH sensor that includes a reference. In this case, both the sensing element portion of the pH sensor and the reference portion of the pH sensor may both include chambers and ports that allow for pressure compensation of both portions. Thus, these sensors do not have to be representatively calibrated, can be used in environments having higher environmental pressures, for example, full ocean depth (e.g., 6000*m*), and offer more stability than conventional pH sensors.

Another embodiment of the sensor module includes a malleable solid material utilized for the pressure compensation. The malleable solid material may be any solid material that will "bend" or "squish" at high pressures. Some non-limiting examples of the malleable solid material include an electronic potting material, epoxy, thermo-plastic, a rubber-like material, a caulk-like material, a very-high viscosity fluid, a near-solid material, or the like. The malleable solid material is positioned under the sensing element in order to support the sensing element when environmental pressures increase on the side of the sensing element exposed to the environment, thereby preventing the sensing element from bending, twisting, or breaking. This embodiment of the sensor module does not require some of the complex mechanical structures present in the sensor module utilizing fluid as the pressure compensation material.

The illustrated example embodiments will be best understood by reference to the figures. The following description is intended only by way of example, and simply illustrates certain example embodiments.

FIG. 1 illustrates an example pH measurement device with pressure compensation 100 utilizing fluid. The configuration as illustrated in FIG. 1 is merely illustrative and it should be understood that the described and illustrated components may be located in different locations than that shown in FIG. 1. Additionally, it should be understood that the measurement device 100 may include greater or fewer components than as shown in FIG. 1.

The pH measurement device 100 may include two or more measurement components. In the illustration of FIG. 1 the measurement device 100 includes two measurement components, a pH sensing component 101 and a reference component 102. The pH measurement device includes a pressure fluid reservoir 103 where pressure compensation fluid can be stored. The pressure compensation fluid may include any non-conductive, non-polar fluid, for example, silicon oil, perfluorinated oil, a gas, or the like. Between the pressure fluid reservoir 103 and the two components, the pH sensing component 101 and the reference component 102, the pH measurement device includes transfer ports 104 and 105. These transfer ports 104 and 105 allow for transfer of the pressure compensation fluid from the fluid reservoir 103 to chambers 106 and 107 within the pH sensing component 101 and the reference component 102, respectively.

The pressure compensation fluid is sealed in the pH measurement device 100 through the use of a plurality of seals or other sealing devices. In the example of FIG. 1, the pH measurement device 100 includes a glass metal seal 108 located between the pressure chamber and a support body of the measurement device. The glass metal seal 108 prevents the pressure compensation fluid from escaping through the bottom of the pH measurement device 100. The pH measurement device 100 also includes two o-rings, or other sealing rings, on the front face of the sensing element or sensing portion to prevent the pressure compensation fluid from escaping through the sensing element. In practice, the glass metal seal and the seals of the sensing element would be sealed and the pressure compensation fluid would be back-filled into the pressure fluid reservoir 103 through a fluid connection 109. A seal diaphragm 110 is then installed between the fluid connection 109 and a pressure port 111. The seal diaphragm 110 may be a small flexible rubber diaphragm, a metal diaphragm (e.g., titanium), or the like. The seal diaphragm 110 is large enough to compensate for any thermal expansion or compression of the fluid. Thus, as the environmental pressure increases and decreases the seal diaphragm 110 moves. Once the seal diaphragm 110 is installed, the pressure compensation fluid is completely sealed within the pH measurement device 100.

When exposed to the environment and environmental pressures, the environmental pressure will be applied to the sensing component 101, the reference component 102, and the pressure port 111. The pressure port 111 transfers the environmental pressure signal to the pressure compensation fluid which causes the pressure compensation fluid to move between the fluid reservoir 103, the reference chamber 107, and the sensing element chamber 106. This transference of fluid causes the chambers 106 and 107 to apply a pressure to the back of the components 101 and 102 that is equal to the pressure that is being applied to the front of the components 101 and 102 from the environmental pressure. Thus, the components are completely supported by the pressure compensation fluid and will, therefore, not bend, warp, or otherwise move due to the environmental pressure. Without the movement the measurements provided by the components 101 and 102 are accurate and do not have to be modified to compensate for the movement of the components as required by traditional sensors. The pH measurement device also includes other components, for example, wires and other electronic components, that transfer signals from one portion of the pH measurement device, for example, the sensing element, to other portions of the pH measurement device, for example, a controller, processor, or other electronic component.

Figure 2:
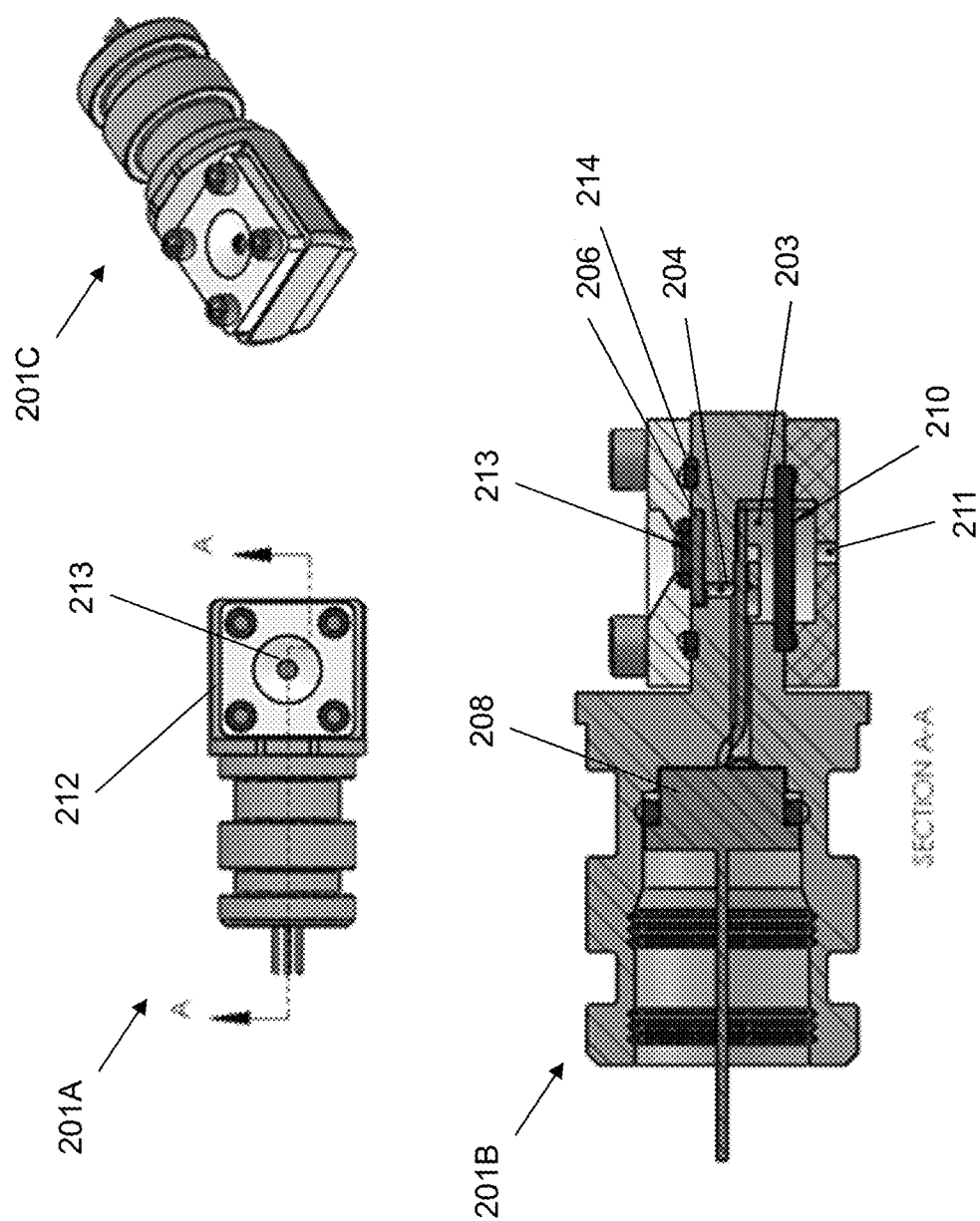
FIG. 2 illustrates an example pressure compensated pH sensing component utilizing fluid.

A larger view of the pH sensing component 101 is illustrated in FIG. 2. FIG. 2 illustrates a top view at 201A, a side view at 201B, and an overall view at 201C. The pH sensing component 101 includes a pH sensing element carrier 212 that includes a pH sensing element 213. When in use, the pH sensing element 213 is exposed to the environment and also to any environmental pressures. Underneath the pH sensing element 213 is a pressure fluid chamber 206. The pressure fluid chamber 206 is of a size that is larger than the sensing element 213 and is located such that the diameter of the pressure fluid chamber 206 overlaps the diameter of the sensing element 213. While the term "diameter" is used, it should be understood that the shapes may not be circular and may instead be square, rectangular, triangular, or any other shape. However, no matter what shape is used, the pressure fluid chamber 206 is of a size and orientation such that the sensing element 213 is completely supported by the pressure fluid chamber 206.

The pH sensing component 101 includes a pressure fluid reservoir 203 that contains the pressure compensation fluid, as explained in connection with FIG. 1. The pressure compensation fluid is sealed within the sensing component 101 through the use of a glass metal seal 208, o-rings at the sensing element 214, and the diaphragm 210. Between the pressure fluid reservoir 203 and the pressure fluid chamber 206 is a transfer port 204 that allows transfer of the pressure compensation fluid between the pressure fluid chamber 206 and the pressure fluid reservoir 203. As the environmental pressure increases, the environmental pressure is applied to the front face of the sensing element 213 and also the pressure port 211. The pressure port 211 transfers this pressure to the pressure compensation fluid which moves between the fluid reservoir 203 and the fluid chamber 206 to support the back of the sensing element 213.

Figure 3:
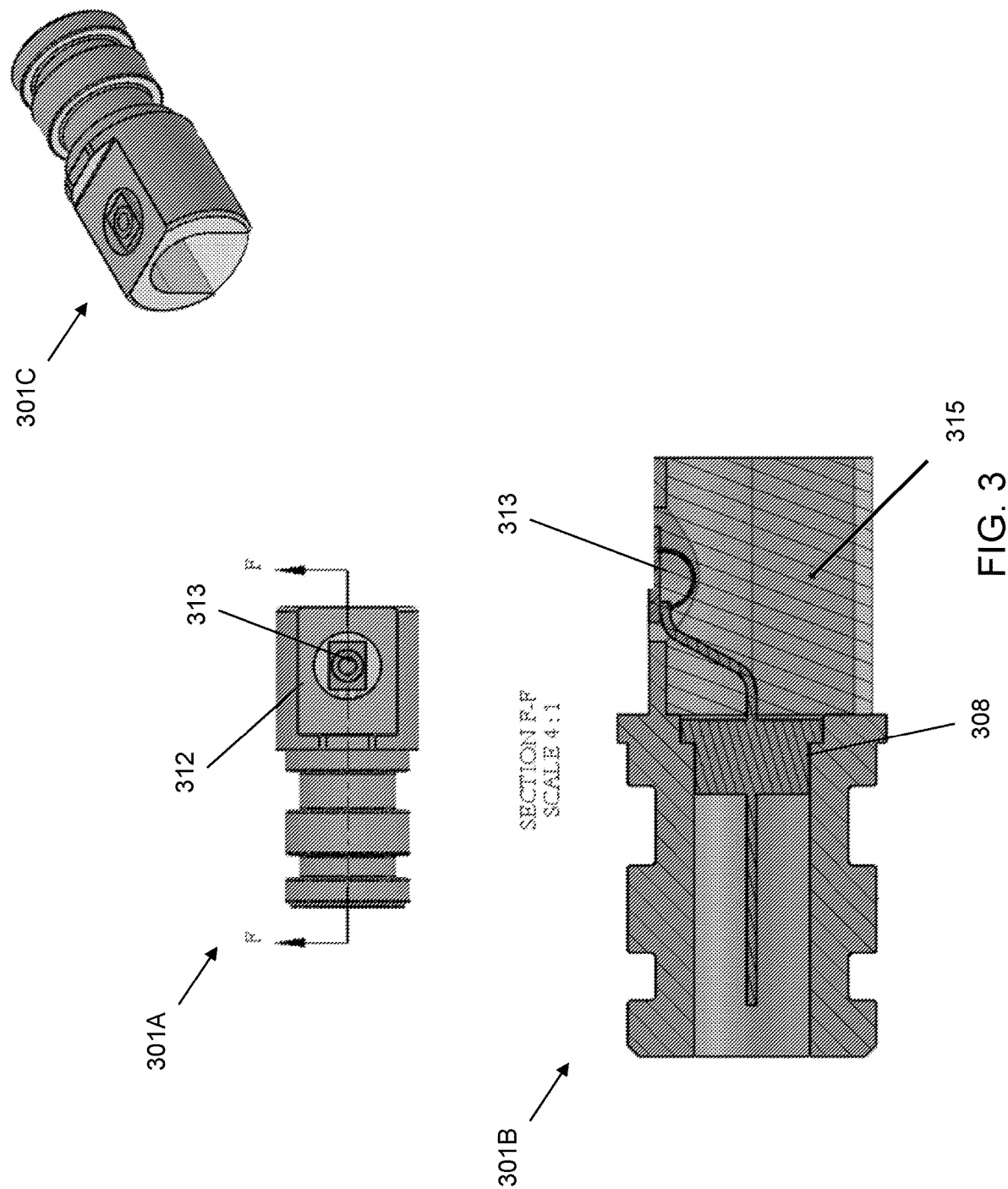
FIG. 3 illustrates an example pressure compensated pH sensing component utilizing a malleable solid material.

FIG. 3 illustrates a sensor module with pressure compensation utilizing a malleable solid material. FIG. 3 illustrates a top view at 301A, a side view at 301B, and an overall view at 301C. Components 308, 312, and 313 are similar to components 208, 212, and 213, respectively, and so will not be discussed in detail again. The use of a malleable solid material 315 allows for elimination of some of the fluid components required in the sensor module of FIGS. 1 and 2. Thus, the FIG. 3 sensor module has fewer components. Rather than requiring fluid ports and fluid holding areas, the malleable solid material 315 is simply provided in a cavity within the sensor module behind the sensing element 313. At increased pressures the malleable solid material behaves similar to a fluid. The malleable solid material may be any material that can move slightly to allow transmission of the pressure signal to the sensing element. Some non-limiting examples of the malleable solid material include an electronic potting material, epoxy, thermo-plastic, a rubber-like material, a caulk-like material, a very-high viscosity fluid, a near-solid material, gel, polyurethane, a soft solid, or the like. The hardness of the material is negligible as compared to the increased pressures, thereby causing the material to behave like a fluid. The pressure is then transmitted through the material to the back of the sensing element 313 so that the sensing element is exposed to the same pressure on both sides of the sensing element, thereby supporting the sensing element 313 so that it does not bend, twist, or break under the increased environmental pressures.

Other components of the pH measurement device are similar to those as described in connection with FIGS. 1 and 2, with the different being that the fluid components of FIGS. 1 and 2 are replaced with the malleable solid material of FIG. 3. It should also be understood that the sensor module may include a combination of the malleable solid material and a fluid, which may include a gas. For example, one type of pressure compensation material may be utilized to support one portion of the sensor module, while another type of pressure compensation material may be utilized to support one portion of the sensor module. Additionally, it should be understood that the sensor modules may be some variation of those illustrated in FIGS. 1-3. These are merely used as illustrative examples and components of the sensor modules may be located in different locations than shown in the figures, the sensor module may have more or fewer components than shown in the figures, and the like.

The various embodiments described herein thus represent a technical improvement to current pH sensors by providing a pressure compensated pH sensor. The pressure compensation allows the pH sensor to be used in environments with high environmental pressures without concern of bending, warping, or movement of the sensing element. Thus, the sensor does not need to be assigned a calibration that accounts for the movement over time. Additionally, since the sensor is pressure compensated, the sensor can be used at full ocean depths, which is not possible with conventional pH sensors. Additionally, since the pH sensors do not have to be representatively calibrated, the measurements are more accurate and remain more stable over measurement cycles.

Figure 4:
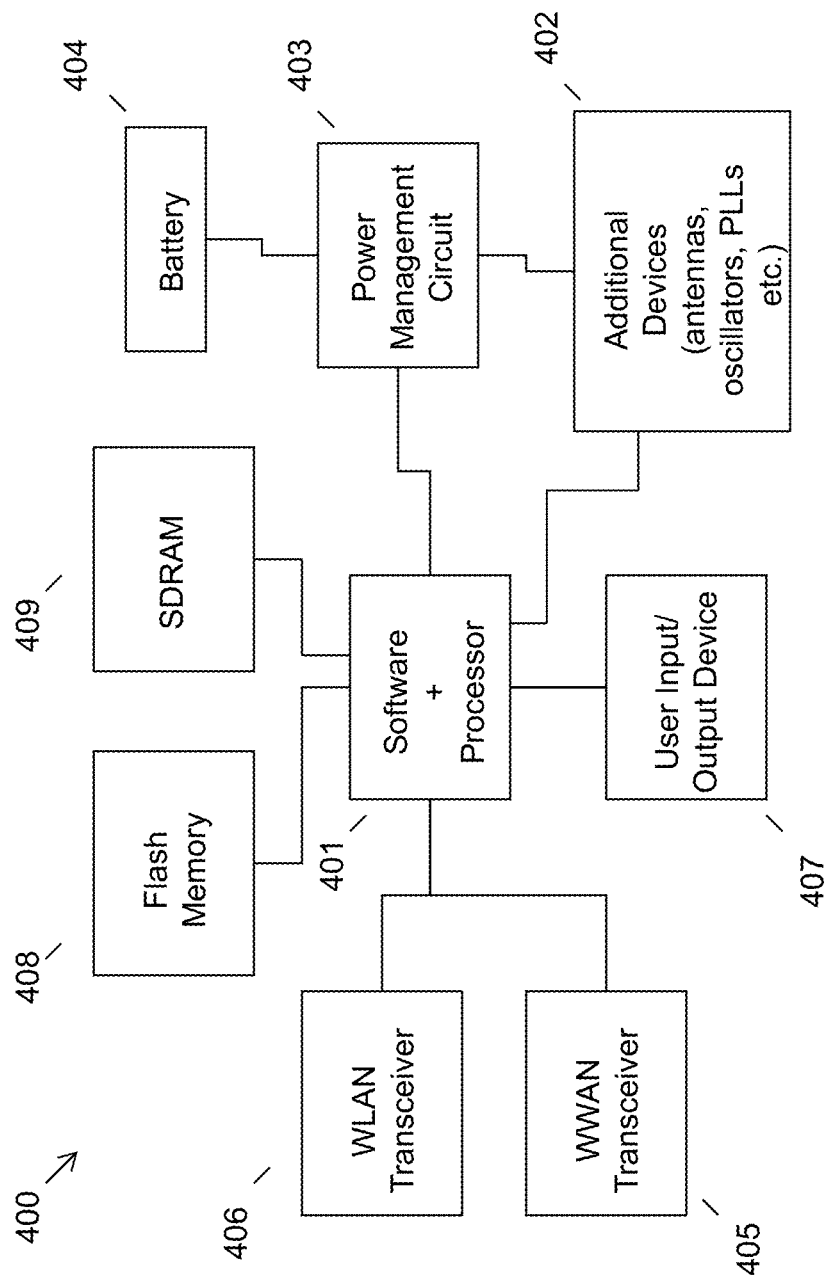
FIG. 4 illustrates an example of computer circuitry.

While various other circuits, circuitry or components may be utilized in information handling devices, with regard to an instrument for measuring fluid level and velocity according to any one of the various embodiments described herein, an example is illustrated in FIG. 4. Device circuitry 400 may include a measurement system on a chip design found, for example, a particular computing platform (e.g., mobile computing, desktop computing, etc.) Software and processor(s) are combined in a single chip 401. Processors comprise internal arithmetic units, registers, cache memory, busses, I/O ports, etc., as is well known in the art. Internal busses and the like depend on different vendors, but essentially all the peripheral devices (402) may attach to a single chip 401. The circuitry 400 combines the processor, memory control, and I/O controller hub all into a single chip 410. Common interfaces may include SPI, I2C and SDIO.

There are power management chip(s) 403, e.g., a battery management unit, BMU, which manage power as supplied, for example, via a rechargeable battery 404, which may be recharged by a connection to a power source (not shown). In at least one design, a single chip, such as 401, is used to supply BIOS like functionality and DRAM memory.

System 400 typically includes one or more of a WWAN transceiver 405 and a WLAN transceiver 406 for connecting to various networks, such as telecommunications networks and wireless Internet devices, e.g., access points. Additionally, devices 402 are commonly included, e.g., an a transmit and receive antenna, oscillators, PLLs, etc. System 400 includes input/output devices 407 for data input and display/rendering (e.g., a computing location located away from the single beam system that is easily accessible by a user). System 400 also typically includes various memory devices, for example flash memory 408 and SDRAM 409.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data.

Embodiments may be implemented as an instrument, system, method or program product. Accordingly, an embodiment may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

A combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device. For the purpose of this disclosure, a storage medium or device is to be construed as non-transitory, i.e., not inclusive of signals or propagating media.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A pressure compensated pH sensor apparatus, comprising:
   a pH sensing component comprising a sensing portion, wherein a face of the sensing portion is directly exposed to a fluid source when in use;
   a pressure chamber located in a position under the sensing portion and that surrounds the sensing portion not exposed to the fluid source when in use;
   a pressure compensation mechanism at least partially located within the pressure chamber, wherein the pressure mechanism reacts to pressure from an environment outside the apparatus, thereby supporting the sensing portion of the pH sensing component by equalizing a pressure caused by the fluid source on the face of the sensing portion and a pressure under the sensing portion, wherein the pressure compensation mechanism comprises a pressure compensation fluid;
   a pressure fluid reservoir for containing at least a portion of the pressure compensation fluid;
   a transfer port located between the pressure chamber and the pressure fluid reservoir that allows transfer of the pressure compensation fluid between the pressure chamber and the pressure fluid reservoir; and
   a pressure port connected to the pressure fluid reservoir, wherein the pressure port transfers pressure from the environment outside the apparatus to the pressure fluid reservoir, thereby causing the pressure compensation fluid to transfer to the pressure chamber and support the sensing portion.

2. The apparatus of claim 1, further comprising at least one sealing ring located between the pressure fluid chamber and the sensing portion.

3. The apparatus of claim 1, further comprising a diaphragm located between the pressure port and the pressure fluid reservoir.

4. The apparatus of claim 1, wherein a pressure applied to the sensing portion via the pressure compensation mechanism is substantially equal to the pressure from the environment outside the apparatus.

5. The apparatus of claim 1, wherein the pressure compensation mechanism comprises a malleable solid material disposed within the pressure chamber, wherein the malleable solid material moves when exposed to pressures from an environment outside the apparatus, thereby supporting the sensing portion.

6. The apparatus of claim 5, wherein the malleable solid material comprises at least one material selected from the group consisting of: electronic potting material, a gel-like material, a rubber-like material, a soft solid, and high-viscosity fluid.

7. The apparatus of claim 1, wherein a cross-sectional dimension of the pressure chamber is greater than a cross-sectional dimension of the sensing portion, the pressure chamber thereby supporting the entirety of the sensing portion.

8. The apparatus of claim 1, further comprising a glass metal seal located between the pressure chamber and a support body of the apparatus.

9. The apparatus of claim 1, wherein the pressure compensation mechanism comprises both a fluid and a malleable solid material.

10. A pressure compensated pH sensor probe, comprising:
    a pH sensing component comprising a sensing portion, wherein a face of the sensing portion is directly exposed to a fluid source when in use;
    a reference component;
    a pressure fluid chamber fluidly located between the sensing portion and the reference component, wherein the pressure chamber surrounds the sensing portion not exposed to the fluid source when in use;
    a pressure compensation mechanism fluidically communicating with the pressure chamber, the sensing portion, and the reference component, wherein the pressure compensation mechanism reacts to pressure from an environment outside the pressure compensated pH sensor probe, thereby supporting both the reference component and the sensing portion of the pH sensing component by equalizing a pressure caused by the fluid source on the face of the sensing portion and a pressure under the sensing portion, wherein the pressure compensation mechanism comprises a pressure compensation fluid;

a pressure fluid reservoir for containing at least a portion of the pressure compensation fluid;

at least one transfer port located between the pressure fluid reservoir and the pressure fluid chamber that allows transfer of the pressure compensation fluid between the pressure fluid chamber and the pressure fluid reservoir; and a pressure port connected to the pressure fluid reservoir, wherein the pressure port transfers pressure from an environment outside the apparatus to the pressure fluid reservoir causing the pressure compensation fluid to support the sensing portion and the reference component.

11. The sensor probe of claim 10, further comprising at least one sealing ring located between the pressure fluid chamber and at least one of: the sensing portion and the reference component.

12. The sensor probe of claim 10, further comprising a diaphragm located between the pressure port and the pressure fluid reservoir.

13. The sensor probe of claim 10, wherein a pressure applied to the sensing portion via the pressure compensation mechanism is substantially equal to the pressure from the environment outside the sensor probe.

14. The sensor probe of claim 10, wherein the pressure compensation mechanism comprises a malleable solid material disposed within the pressure chamber, wherein the malleable solid material moves when exposed to pressures from an environment outside the apparatus, thereby supporting the sensing portion and the reference component.

15. The sensor probe of claim 14, wherein the malleable solid material comprises at least one material selected from the group consisting of: electronic potting material, a gel-like material, a rubber-like material, a soft solid, and high-viscosity fluid.

16. The sensor probe of claim 10, wherein a cross-sectional dimension of the pressure chamber is greater than a cross-sectional dimension of the sensing portion, the pressure chamber thereby supporting the entirety of the sensing portion.

17. The sensor probe of claim 10, further comprising a glass metal seal located between the pressure chamber and a support body of the sensor probe.

18. The sensor probe of claim 10, wherein the pressure compensation mechanism comprises both a fluid and a malleable solid material.

* * * * *